United States Patent [19]

Bentley et al.

[11] 4,183,357

[45] Jan. 15, 1980

[54] CHRONIC TRANSCUTANEOUS IMPLANT ASSEMBLY FOR ENTEROSTOMIES

[75] Inventors: Donald J. Bentley, Newport Beach; James A. Benson, Tustin, both of Calif.

[73] Assignee: Bentley Laboratories, Inc., Irvine, Calif.

[21] Appl. No.: 921,707

[22] Filed: Jul. 3, 1978

Related U.S. Application Data

[63] Continuation of Ser. No. 710,638, Aug. 2, 1976, abandoned, which is a continuation-in-part of Ser. No. 525,832, Nov. 21, 1974, abandoned, which is a continuation-in-part of Ser. No. 338,051, Mar. 1, 1973, abandoned.

[51] Int. Cl.² .................................................. A61F 5/44
[52] U.S. Cl. .................................................. 128/283; 3/1
[58] Field of Search ................... 3/1, 1.1, 13; 128/1 R, 128/2 R, 214 R, 283, 334 R, 334 C, 348, 350 R, 351, 419 P

[56] References Cited

U.S. PATENT DOCUMENTS

| | | | |
|---|---|---|---|
| 2,818,069 | 12/1957 | Fenton | 128/283 |
| 3,216,420 | 11/1965 | Smith et al. | 128/283 |
| 3,646,616 | 3/1972 | Keshin | 128/283 |
| 3,663,965 | 5/1972 | Lee, Jr. et al. | 3/1 |
| 3,774,615 | 11/1973 | Lim et al. | 128/334 C |

Primary Examiner—Robert W. Michell
Assistant Examiner—C. F. Rosenbaum
Attorney, Agent, or Firm—Lyon & Lyon

[57] ABSTRACT

A chronic transcutaneous implant device for enterostomies is disclosed. The implant device is comprised of a barrel portion and flange portion. The barrel portion is provided with means to enable vascularization of the externalized vessel and the flange portion is provided with means to enable the formation of a vascularized biological anchor. The implant device is capable of being permanently positioned under the skin. The implant device is provided with a detachable bag member which functions to receive excrements exiting the externalized vessel.

4 Claims, 6 Drawing Figures

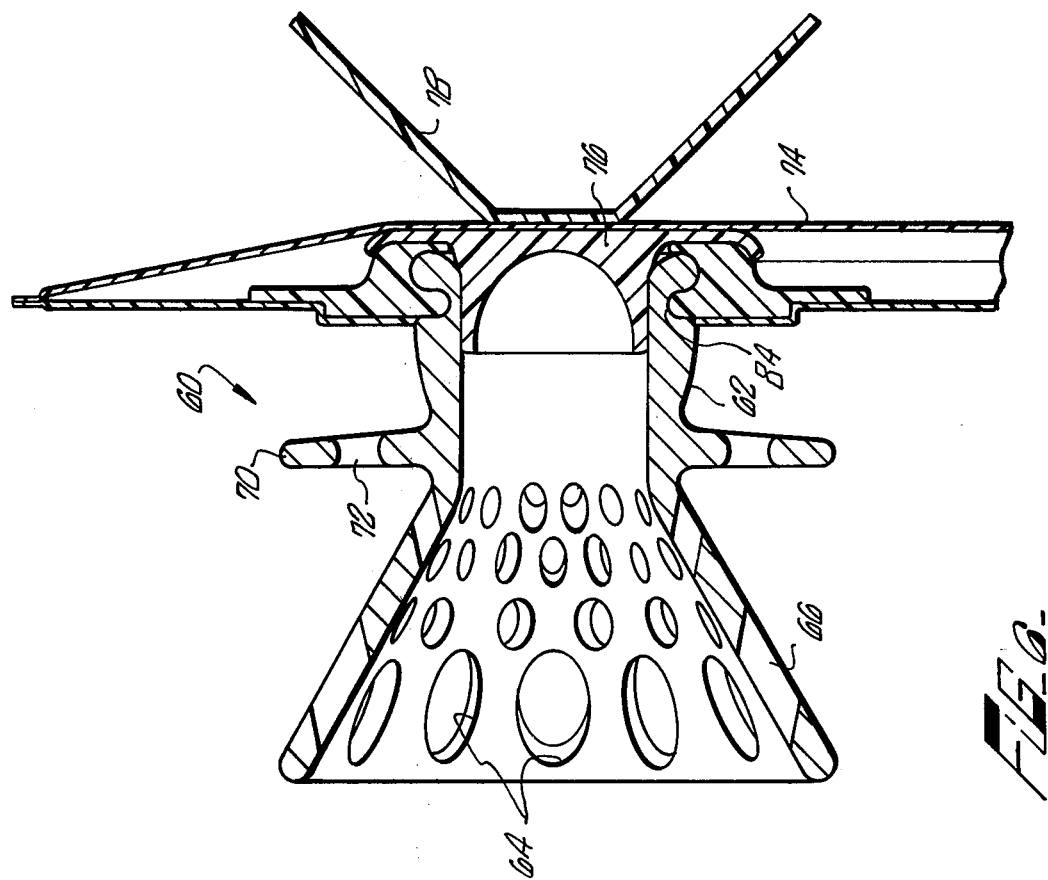

CHRONIC TRANSCUTANEOUS IMPLANT ASSEMBLY FOR ENTEROSTOMIES

BACKGROUND OF THE INVENTION

The present application is a continuation of our U.S. patent application Ser. No. 710,638 which was filed Aug. 2, 1976, which was a continuation-in-part of our U.S. patent application Ser. No. 525,832, filed Nov. 21, 1974, which was in turn a continuation-in-part of our U.S. patent application Ser. No. 338,051, filed Mar. 1, 1973, said U.S. patent application Ser. Nos. 710,638, 525,832 and 338,051 now being abandoned.

The present invention relates to a chronic transcutaneous implant device, and, in particular, relates to a chronic transcutaneous implant device which functions as a conduit means for externalizing internal vessels or organs.

There are many situations in which it is necessary to perform an enterostomy on a patient. An enterostomy involves externalizing an internal vessel or organ. The most common vessels or organs which may require externalizing are the ileum, color, ureter, urethra, and the bladder and pelvis of the kidney. Heretofore, enterostomies were accomplished by severing the vessel which was to be externalized or creating a tube from the wall of the organ which was to be externalized and then suturing the wall of the vessel or tube to an opening which had been formed on the surface of the body. The opening was normally formed on the abdomen. Generally, the wall of the vessel and the dermis of the skin surrounding the opening would grow together to permanently secure the vessel to the surface of the body. After the operation was healed, a container was attached to the surface of the skin. The container functioned to receive the excrements which were discharged from the vessel. These excrements were normally corrosive due to the presence of enzymes, etc., and when they contacted the surface of the skin, they caused ulceration. For example, in an illeostomy, the ileum was externalized to the abdomen of the patient and the enzymes, urine, etc., which exited from the ileum caused ulceration of the skin surrounding the point of externalization. This was primarily due to the presence of active enzymes in the small intestines.

SUMMARY OF THE INVENTION

It is therefore an object of the present invention to provide a chronic transcutaneous implant device for use in enterostomies which will prevent the excrements which are being discharged from the externalized vessel or organ from contacting the surface of the skin.

It is a further object of the resent invention to provide a chronic transcutaneous implant device for use in enterostomies which will enable vascularization of the externalized vessel or organ.

These and other objects and advantages are obtained by forming a chronic transcutaneous implant device. The implant device is provided with a first means to enable vascularization of the externalized vessel thereby preventing necrosis of the vessel. It is preferred that the first means comprise a barrel portion having a plurality of apertures which enable the ingrowth of the tissue of the externalized vessel through the implant into the dermis thereby forming a vascularized connection for the vessel. The implant device is further provided with a second means to enable the formation of a vascularized biological anchor and a seal between the device and the dermis. It is preferred that the second means comprises a flange portion having a plurality of apertures which enable the ingrowth of vascularized dermis tissue to form a secure biological anchor for the implant. In an alternative embodiment, limited areas of porous material can be substituted in place, and at the location of, the apertures formed in the first and second means. The porous material preferably has pore sizes of approximately 20 to 100 microns and each pore has an entrance and an exit such that there are no dead spaces within the material. A bag member is preferably detachably attached to the implant device to receive excrements exiting the externalized vessel.

BRIEF DESCRIPTION OF THE DRAWINGS

A more thorough disclosure of the objects and advantages of the present invention is presented in the detailed description which follows and from the accompanying drawings of which.

DETAILED DESCRIPTION OF THE INVENTION

Figure 1:
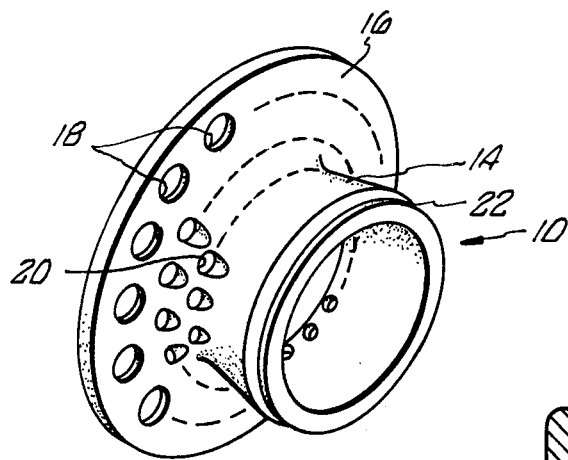
FIG. 1 is a perspective view of the implant device.

The present invention contemplates the formation of a chronic transcutaneous implant device having a detachable bag member. The implant device is preferably comprised of a barrel portion which is integrally formed with a flange portion. The barrel portion is provided with means to enable vascularization of the externalized vessel thereby preventing subsequent necrosis of the vessel. It is preferred that the means comprise a plurality of apertures. The apertures enable ingrowth of the tissue of the vessel through the implant into the dermis to form a vascularized connection for the vessel and a seal between the vessel and the inside of the implant device. The flange portion is provided with means to enable the formation of a vascularized biological anchor. It is preferred that the means also comprise a plurality of apertures. The apertures formed on the flange portion function to enable the ingrowth of dermis tissue from both faces of the flange when the implant is partially positioned under the skin. The dermis tissue eventually grows together to form a secure vascularized biological anchor for the implant. The apertures formed in the barrel and flange are preferably round holes but can be slots or irregularly shaped holes. In an alternative embodiment, limited areas of porous material can be substituted in place of the apertures formed in the barrel and flange. The porous material may be positioned at the same location as the apertures and extends through the entire thickness of the wall of the device. The material is preferably impermeable and nonabsorbent and a suitable material for the practice for the practice of the present invention consists of carbon. The porous material preferably comprises a plurality of pores formed so that each pore has an entrance and an exit thereby preventing necrosis which is caused by the ingrowth of tissue into dead end pores. The pores are preferably formed having a pore diameter of approximately 20 to 100 microns. Suitable porous material can be formed utilizing the process disclosed in the White, et al, U.S. Pat. No. 3,890,107, but it will be obvious to one skilled in the art that other processes can also be utilized to form porous material suitable for the practice of the present invention. It will also be obvious to one skilled in the art that other means may also be utilized to enable the vascularization of the externalized vessel or organ and the dermis tissue.

The implant device is preferably combined with a disposable detachable bag member which functions to receive excrements exiting the externalized vessel. In the case where the internal organ is formed with a natural reservoir, the bag member may be provided with a plug member. The plug member is insertable into the barrel portion of the device and functions to prevent excrements from exiting the externalized organ or vessel. The plug member may be removed at an appropriate time to enable the discharge of excrements into an appropriate receptable.

The implant device is comprised of a material which is non-absorbing, impermeable, biocompatible and non-biodegradable. The implant device is, thus, capable of being partially positioned, in a permanent fashion, below the surface of the skin without causing tissue reaction infections or rejection by the body.

It is also important that the material of the implant device be essentially non-porous, except in areas of intended attachment or vascularization, to enable the discharge of waste products along the surface of the device so that the waste products do not impregnate the device and cause necrosis of adjacent tissue.

The implant device is preferably formed from substantially pure polymeric carbon such as a highly polished vitreous (glassy) carbon or from pyrolytic carbon disposed on a graphite or other substrate. Pure carbon is a nonbiological solid that is completely biocompatible; that is, there appears to be no recognition of or reaction to pure carbon by living tissue. In addition, carbon is not degraded or changed by a biological environment and, therefore, no degradation products are created to cause reactions. Preparation of a vitreous carbon is now well-known in the art. The vitreous (glassy) carbon is non-crystalline but it is also possible to use a crystalline carbon, such as graphite. It will, however, be apparent to those skilled in the art that the implant device can be comprised of other nonporous, biocompatible and non-biodegradable materials such as plastic or ceramic materials.

Figure 3:
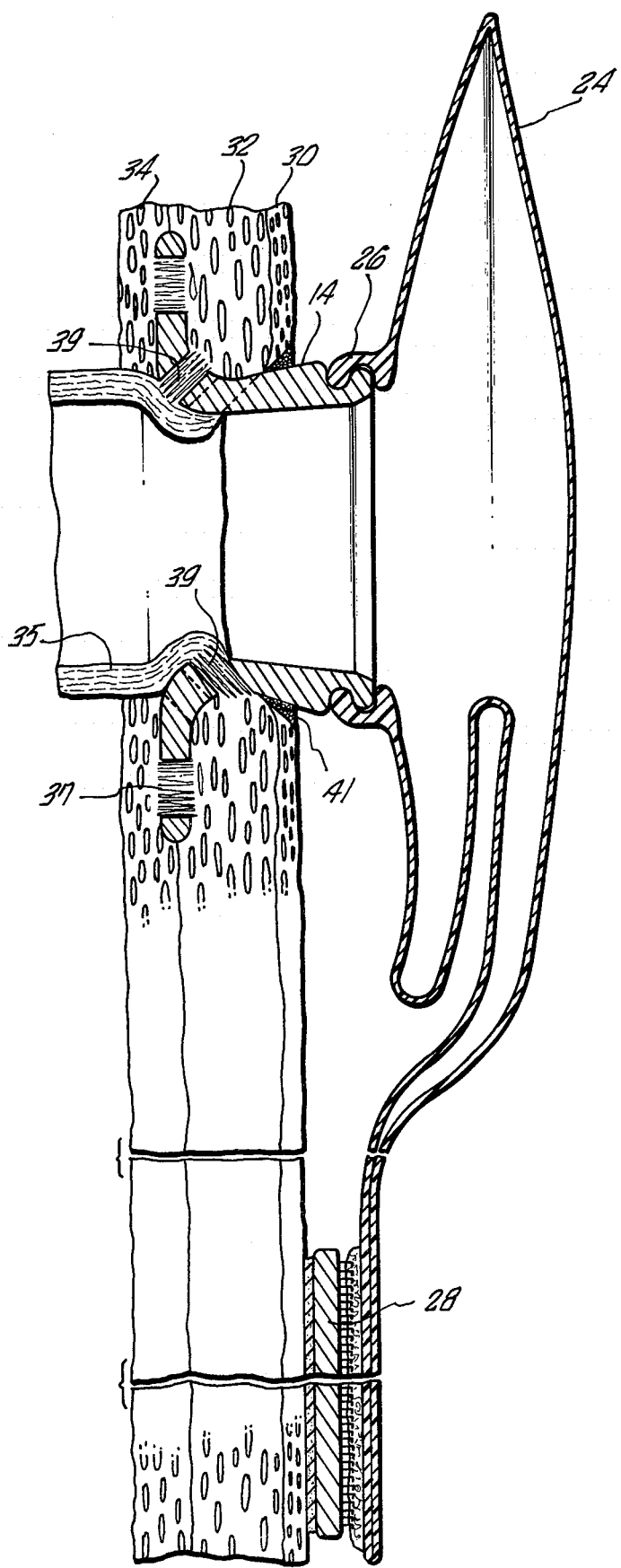
FIG. 3 is a cross sectional view of the implant device with the associated bag member after the operation is healed.

Referring now to FIGS. 1 and 3, there is shown the preferred embodiment of the implant device 10. The implant device is preferably comprised of a hollow barrel 14 integrally formed with flange 16. A plurality of apertures 18 is formed in the flange 16. A plurality of apertures 20 is formed in barrel 14. The apertures 20 may be positioned in any random pattern but are preferably positioned in two offset rows. The apertures 20 are preferably formed at a 45° angle so that they slope down into the interior of the barrel and are preferably formed only on the lower portion of barrel 14. The distal portion of barrel 14 is provided with annular groove 22. The implant device is provided with a bag member 24 which consists of an elastomer which is impermeable to odors. The bag member 24 is provided with elastic ring 26 and support member 28. The elastic ring 26 is capable of detachable attachment with barrel 14 of the implant device by inserting the ring over the barrel until it engages annular groove 22 of the barrel. The support member 28 is capable of attachment to the body and is preferably an adhesive ring or belt. The support member 28 functions to bear the weight of the bag and contents to prevent traumatizing the skin surrounding the implant member.

The implant device is shaped to encourage the growth of the epithelium inwardly along the surface and encourage outward discharge of dead skin or keratin along the surface of the implant. The shape of a preferred embodiment of the implant device 10 which permits early healing and results in less easily traumatized installation is shown generally in the drawings and may be defined by a surface of revolution which is approximated by the following:

In polar coordinates, the equation of the lateral surface of the preferred embodiment is:

$$R = R_o = f(h)$$

Where R is the radius, H is the total height, and h is the distance from the top of the implant.

For $h \leq 0.6H$; $(x = h/H)$ $$f = H(0.1 + 1.28x - 7.38x^2 + 14.6x^3 - 12.83x^4 + 4.28x^5)$$

For $h \leq 0.6H$; $(x = h/H)$ $$f = H(-3.2x + 35.7x^2 - 121.2x^3 + 159.0x^4 - 69.5x^5)$$

The implant device may be extremely small, when it is visualized that the thickness of the skin is only a few millimeters thick in the areas at which the implant device would e implanted. The foregoing equation of the lateral surface in polar coordinates provides the shape of implant device shown in the drawings and with a general ratio of parts of the implant device as shown in FIG. 4.

Figure 4:
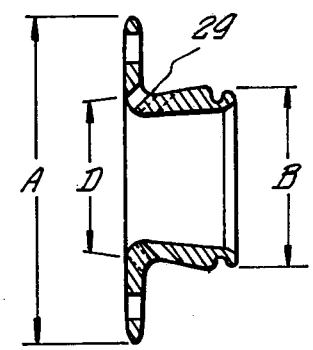
FIG. 4 is a cross sectional view of the implant device.

In FIG. 4, B expresses a major diameter at the upper end of the implant device and is selected dependent upon the exact function of the implant device. C (not shown) defines the thickness of the dermis and epidermis combined. Reference letter A identifies the major diameter of the implant device including the flange 16. A has the ratio to B and C as follows:

$$A = B + 3C$$

The reference letter D identifies the minimal diameter of the curved contour 29 and D has the following relation:

$$D = B - (2\frac{2}{C})$$

The upper exposed part of the implant device would normally be a minimum of one-half millimeter to a maximum of C/2. The upper sloped surface of the flange 16 is sloped from the plane of the base at an angle of approximately 5° and with the curve at the end of the flange defined by $R_1$ as well as $R_1$ at the upper exposed end equalling approximately one-half millimeter. Reference letter $R_2$ defines the curve connecting the concavely-curved section, with the upper sloped wall of the flange 16 and would be defined as follows:

$$R_2 = C/4$$

The implant device 10 is inserted into the skin through an opening formed in the body of the patient. The skin is comprised of two layers. The outer layer is known as the epidermis or keratin 30 and is comprised of old, dry, scale-like cells which are continuously flaking off. The inner, second layer of skin is the dermis 32. The dermis 32 is comprised of a layer of fibrous-type tissue interspersed with capillaries. The dermis overlies the facia 34, which is a fatty tissue interspersed with capillaries. The facia 34 perform several essential functions such as providing nourishment to the dermis and insulation to the body.

Figure 2:
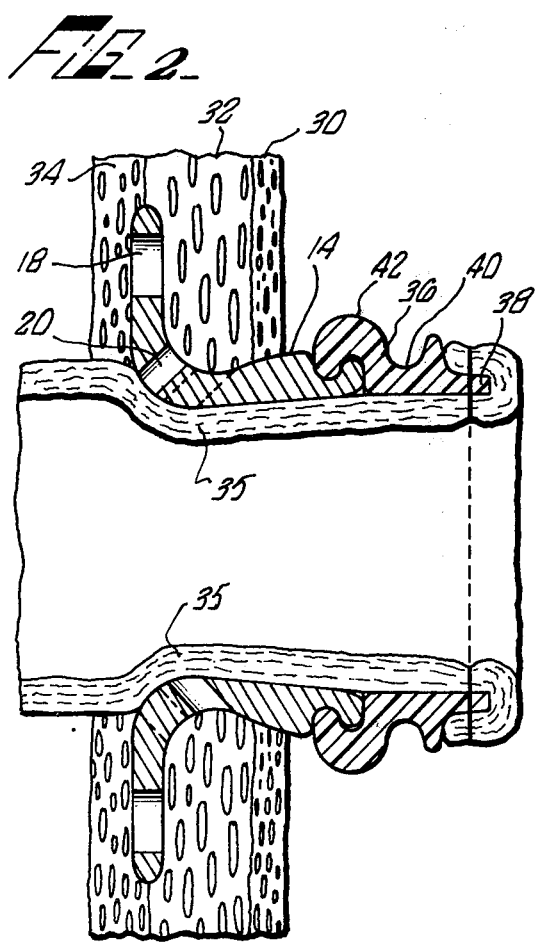
FIG. 2 is a post operative cross-section of the implant device positioned within the skin of the patient.

As shown in FIG. 2, one method of performing an enterostomy comprises first attaching a suture ring or sewing ring 36 to the implant device. The suture ring 36 preferably consists of polyurethane and is comprised of collar 38, annular groove 40 and flange 42 which is capable of locking engagement with groove 22 of barrel 14. The implant device is then inserted into the skin so that flange 16 is positioned between the dermis 32 and facia 34 and the lower portion of the barrel 14 is contiguous to the dermis 32 and epidermis 30. The distal part of barrel 14 extends out of the body of the patient. Vessel 35 is then drawn up through hollow barrel 14 and suture ring 36. The vessel is then folded over the suture ring and sutured to the collar 38. A detachable bag member similar to the bag member 24 shown in FIG. 3 is then attached to groove 40 of suture ring 36 to receive excrements exiting the externalized vessel.

During the healing process, the dermis tissue surrounding the implant grows into intimate contact with the carbon surface so that the dermis tissue integrally interfaces the carbon surface to form a permanent tight seal around the implant. A fibrous connective tissue grows into and through the apertures 18 and 20 to completely fill the apertures with the tissue and complete a vascular pathway through the apertures. As shown in FIG. 3, with the ingrowth of the vascularized fibrin tissue 37 into apertures 18, a secure biological anchor is formed and the implant device becomes securely attached to the body. The ingrowth of a vascularized fibrin tissue 39 through apertures 20 and onto the vessel provides a vascular pathway for the externalized vessel and securely attaches the outer wall of the vessel to the dermis. Apertures 20 may be formed at a 45° angle with respect to the wall of barrel 14 to facilitate attachment of vessel 35 to the dermis 32 and to avoid the stress which would result from a 90° connection.

After the formation of the vascularized fibrin tissue, the distal portion of vessel 35 will become atrophied beyond the distal row of apertures 20. This is due to the formation of the new vascular pathway through apertures 20 and the subsequent change in the blood flow pattern which results in blood flowing only through the new vascular pathway. As shown in FIG. 3, the distal portion of vessel 35 is removed after it has atrophied. The suture ring 36 is then removed and the bag member 24 is attached directly to barrel 14 of the implant device. FIG. 3 also shows the keratin ring 41 being discharged along the surface of barrel 14 of the implant.

Figure 5:
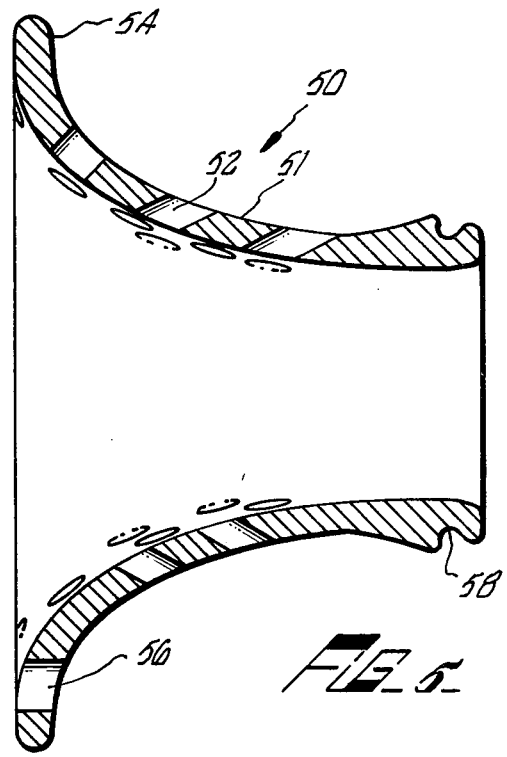
FIG. 5 is a cross sectional view of an alternate embodiment of the implant device; and, FIG. 6 is a cross sectional view of another alternate embodiment of the implant device.

In FIG. 5 is shown an alternate embodiment of the implant device according to the present invention. The device is designed to enable the externalization of an organ such as a bladder which is not formed in the shape of a vessel. The implant 50 is preferably generally bell-shaped comprising an annular wall 51 having a plurality of apertures 52. The wall 51 is integrally formed with flange 54 having apertures 56 formed therein. The wall is also provided with an annular groove 58 which functions as a point of attachment for a bag member.

The device is implanted into an organ such as the bladder with the flange 54 protruding into the muscle sheath below the dermis. Because the device is implanted into the muscle sheath below the dermis and facia, it is formed with a greater length than implant devices used for externalizing vessels. Before the device is implanted, the wall of the organ preferably is traumatized to promote ingrowth of vascularized tissue into the apertures formed in the device. An opening is then formed in the wall of the bladder and the wall is pulled through the interior of the device and securely sutured to a detachable suture ring which is attached to groove 58 of the device.

With healing, the vascularized muscle tissue will grow through apertures 56 to form a secure vascularized biological anchor for the device and the wall of the bladder will grow through the aperture 52 and into the dermis to form vascularized connection for the bladder.

In FIG. 6, there is shown another alternate embodiment of the implant device which is designed to enable the externalization of an organ such as a bladder. The implant 60 is comprised of a generally funnel-shaped barrel 62 having annular groove 64 formed therein. The base 66 of barrel 62 is flared outwardly and is preferably provided with a plurality of apertures 68. The barrel 62 is provided with flange 70 which is spaced away from the end of the barrel and is provided with a plurality of apertures 72 formed therein. The barrel 62 is further provided with annular groove 64 which functions as a point of attachment for bag member 74. Bag member 74 is provided with a plug 76 which is preferably comprised of a resilient biocompatible and non-biodegradable polymeric material and is attached to the wall of the bag 74. The plug 74 is insertable into barrel 62 and is preferably a chevron plug with flared edges to enable retention of the plug in barrel 62. The plug is provided with grasping means 78 to enable its insertion and removal from barrel 62.

The implant device 60 is implanted into an organ such as the bladder by first exposing the bladder and then forming an opening in the wall of the bladder. The base 66 of the implant is inserted into the bladder and the wall of the bladder is sutured to base 66 through apertures 64. The flange 70 of the implant is then positioned between the dermis and the facia and sutured therein through apertures 72.

With healing, the vascularized muscle tissue will grow through apertures 72 to form a secure vascularized biological anchor for the implant and the wall of the bladder will grow through the aperture 64 to secure the bladder to the base of the implant.

After healing, bag member 74 is attached to groove 84 of implant 60. Since the bladder is a natural reservoir for urine, plug 76 can be inserted into barrel 62 to retain the urine within the bladder until an appropriate time for removal. The bag member may also be provided with a second opening to enable simultaneous discharge of the urine into an appropriate receptacle.

While an embodiment and application of this invention have been shown and described, it will be apparent to those skilled in the art that many more modifications are possible without departing from the inventive concepts herein described. The invention, therefore, is not to be restricted except as is necessary by the prior art and by the spirit of the appended claims.

We claim:

1. A chronic transcutaneous substantially non-absorbing, impermeable, biocompatible and non-biodegradable implant device comprising:
    a barrel member open at each end, said barrel member being further defined as including at least one annular groove at one end thereof;
    a flange member extending from and secured to the exterior of said barrel member, said flange member including a plurality of apertures; and
    a suture ring attached about said barrel member annular groove and extending longitudinally from said barrel member.

2. The implant device of claim 1 wherein said barrel and flange consist essentially of a polymeric carbon.

3. The implant device of claim 1 wherein said barrel is flared at one end and said flange is located along the length of said barrel.

4. An implant device as defined in claim 1, wherein the external shape of the body is a surface of revolution and having a lateral surface substantially as defined by the equation $R = R_o + f(h)$ in polar coordinates:
    where R is the radius, H is the total height, and h is the distance from the top of the implant;

For $h \leq 0.6H$; $(x = h/H)$ $f = h(0.1 + 1.28x - 7.38x^2 + 14.6x^3 - 12.83x^4 + 4.28x^5)$ For $h \leq 0.6H$; $(x = h/H)$ $f = H(3.2x + 35.7x^2 + 159.0x^4 - 69.5x^5)$.

* * * * *